United States Patent

Teller et al.

[11] Patent Number: 5,759,376
[45] Date of Patent: Jun. 2, 1998

[54] METHOD FOR THE ELECTRODEPOSITION OF HYDROXYAPATITE LAYERS

[75] Inventors: Joachim Teller, Mistorf; H. Georg Neumann, Rostock, both of Germany

[73] Assignee: Dot Dunnschicht- Und Oberflaechen-technologie GmbH, Rostock, Germany

[21] Appl. No.: 809,056

[22] PCT Filed: Sep. 6, 1995

[86] PCT No.: PCT/EP95/03499

§ 371 Date: Mar. 7, 1997

§ 102(e) Date: Mar. 7, 1997

[87] PCT Pub. No.: WO96/07438

PCT Pub. Date: Mar. 14, 1996

[30] Foreign Application Priority Data

Sep. 7, 1994 [DE] Germany ............... 44 31 862.6

[51] Int. Cl.$^6$ ............................ C25D 9/08
[52] U.S. Cl. ............... 205/50; 204/486; 204/487; 204/108; 204/188; 204/189; 204/318; 623/16; 623/901
[58] Field of Search .................. 205/108, 188, 205/189, 318, 50; 623/16, 901; 204/486, 487, 490, 491

[56] References Cited

U.S. PATENT DOCUMENTS 5,211,833  5/1993  Shirkhanzadeh ............... 205/322
5,310,464  5/1994  Redepenning ............... 204/180.2
5,470,668  11/1995  Wu et al. ............... 428/688
5,643,447  7/1997  Lev et al. ............... 210/198.3

FOREIGN PATENT DOCUMENTS 2073781    1/1994  Canada.
WO93/21969 11/1993  WIPO.

*Primary Examiner*—Kathryn L. Gorgos
*Assistant Examiner*—William T. Leader
*Attorney, Agent, or Firm*—Jordan and Hamburg

[57] ABSTRACT

The invention concerns a method for the electrochemical deposition of hydroxyapatite layers onto metal and ceramic surfaces, the actual electrochemical coating being combined with a pre-coating of the substrates by sol-gel processes, using a calcium and (hydrogen) phosphate-containing electrolyte by means of pulsed direct current. Materials coated in this way are used in the form of biocompatible implants in human and veterinary medicine and are distinguished by particularly high grow-in rates. In contrast to conventional methods of generating hydroxyapatite layers (conventional or microwave sintering of hydroxyapatite produced by the wet-chemical method, deposition by other electrochemical, plasma or laser-aided methods or by sol-gel techniques), this method is distinguished by the application of uniform hydroxyapatite coatings which adhere well and have a small amorphous portion and an optimum layer thickness (5–25 μm) whilst requiring comparatively low expenditure in terms of apparatus, energy, time and material.

20 Claims, No Drawings

METHOD FOR THE ELECTRODEPOSITION OF HYDROXYAPATITE LAYERS

This is a national stage application of PCT EP95/03499, filed on Sep. 6, 1995.

The invention relates to a method for electrodepositing hydroxyapatite layers of the general composition $Ca_{x+9}(PO_4)_{x+5}(HPO_4)_{1-x}(OH)_{x+1}$, in which x represents a value between zero and 1, on metal surfaces and ceramic surfaces. Materials, coated in this manner, are used in the form of biocompatible implants in human and veterinary medicine, which are distinguished by particularly high growing-in rates. Various methods have already been described for producing hydroxyapatite and other calcium phosphate coatings. However, all of them are afflicted with certain deficiencies.

The already established methods include plasma spraying of hydroxyapatite[1]. Although this method is comparatively expensive, it has not been possible, because of the line-by-line or the side-by-side application, to produce coatings, which are uniform in relation to the thickness, adhesion and homogeneity of the layer if substrate geometries are somewhat complicated. Hydroxyapatite coatings with consistently lower adhesion can be prepared by drying[2], conventional sintering[3] or microwave-sintering[4] of hydroxyapatite, produced by methods involving wet chemistry or deposited from suspensions. Expensive (vacuum) sintering processes for producing uniform coatings are also characteristic of the sol-gel[5] and the electrophoresis[6] methods. On the other hand, a high technical effort for the actual coating process characterizes methods, which are based on the sputtering technique[7] and the pulsed laser deposition process[8]. An electrochemical method[9], which is suitable for coating mechanically pretreated surfaces of titanium (alloy) substrates with calcium phosphate, can be realized more easily technologically. A more uniform layer growth is said to be achieved by using pulsed direct current[10,11] (20 sec on-off cycle; direct current as in the original method. However, the adhesion of the calcium phosphate layer to the titanium substrate is not increased significantly by these means.

It is an object of the present invention to develop a method for depositing hydroxyapatite on metal, alloy and ceramic surfaces, which is distinguished by a uniform, well adhering coating of optimum thickness and by a low proportion of amorphous materials, while the expenditure for equipment, energy, time and material is relatively small.

Pursuant to the invention, this objective is accomplished owing to the fact that the actual electrochemical coating process, using an electrolyte containing calcium phosphate and calcium hydrogen phosphate and a pulsed direct current of suitable frequency, is preceded by a preliminary coating process using a sol-gel technique. The sol-gel couting is a mutual approximation of the chemical composition of the substrate and of the hydroxyapatite layer because the solution used for the sol-gel coating has elements of the chemical composition of the substrate and/or the hydroxyapatite layer. As a result of the solution used for the sol-gel coating including elements of the substrate and/or the hydroxyapatite coating layer, there is a significant increase in the adhesion of the hydroapatite coating layer. The increase in adhesion is achieved by the number as well as the type of solutions used. With respect to the areas of application of the invention, the substrates themselves, which are to be coated, should have sufficient biocompatibility. This concerns, in the case of the metals, for example, titanium and platinum, in the case of alloys, various iron and nonferrous metal alloys, particularly high-grade steels, CoCr28Mo and TiA16V4, and, in the case of ceramic materials, predominantly oxides, nitrides, oxynitrides and carbonitrides, which contain, in their composition, one or more metals from the and groups 4 and 5 of the periodic system of the chemical elements. The substrates to be coated consist either completely or partly of the materials given above or these materials, in the form of monolayer or multilayer coatings on basic objects of metal, alloys, ceramics, glasses or plastics, are a component of the substrates. The substrates are pretreated by a sol-gel coating using alkoxides, which contain an element of groups 3–5 and 13–15 of the periodic system of the chemical elements, or mixtures of such alkoxides, which optionally contain calcium phosphate ions and/or calcium hydrogen phosphate ions or esters of phosphoric acid as further components, by means of one or several applications by spraying, ultrasonic fogging or by the dip coating method. It is also possible to carry out the preliminary treatment by a sequence of (electro)chemical passivation and sol-gel coating.

The pretreated substrates are coated electrochemically in an electrolysis cell, which is equipped with the usual equipment for tempering and for mixing the electrolytes, the calcium phosphate ions and the calcium hydrogen phosphate ions in a molar ratio of approximately 1.5 to 1.7, an inert anode, for example of carbon, gold or platinum, and the substrate itself as substrate, using a pulsed direct current with a pulse frequency between 1 and 300 Hz and preferably of 50 Hz with identical on-off intervals, and a voltage of 2 to 10 V. Optimum temperatures for the quality of the coating fall within the range of 20° to 40° C. The coatings, so prepared, are usually washed with deionized water and dried in a stream of air, which optionally is pre-heated. Furthermore, tempering of the coated substrates at temperature between 300° and 500° C. is possible but not absolutely essential. If such a thermal treatment is carried out, it is associated with the useful effect that the coating contains carbonates proportionally.

The coatings, prepared pursuant to the invention, can be sterilized by conventional methods.

The thickness of the hydroxyapaptite deposition can be varied by varying the electrolyte concentration and the remaining pretreatment and process parameters and, for typical applications, is of the order of 5 to 25 µm. With that, a covering density of 1 to 3 $mg/cm^2$ is achieved.

The advantage of the invention lies therein that, by the method above, hydroxyapatite can be deposited on metal and ceramic surfaces of the type, required for use as biocompatible implants in human and veterinary medicine. Moreover, the application of uniform, well adhering hydroxyapatite layers, containing a small proportion of amorphous materials and having a thickness optimum proportions, is assured by a sol-gel pretreatment.

The invention is described in greater detail in the following by means of examples, which are given by way of illustration and not by way of limitation.

EXAMPLE 1

A titanium panel, having the dimensions of 80×10×1.5 mm, is cleaned in an ultrasonic bath with a 1:1 mixture of isopropanol and acetone. Using the dip coating technique (withdrawing rate of 1 cm/min), the surface is subjected twice to a sol-gel coating procedure, using a solution consisting of 0.05 moles/L of $Ti(i-C_3H_7O)_4$, 0.05 moles/L of $Si(OC_2H_5)_4$ and 0.1 moles/L of HCl in the form of 37% hydrochloric acid for the first treatment and 0. 05 moles/L of phosphoric acid in the form of 85% phosphoric acid for the second treatment in isopropanol. About 6 hours later, the hydroxyapatite is deposited electrochemically in a glass cell having a capacity of 100 mL using the pre-coated titanium panel as the cathode and using a carbon anode. A solution consisting of 0.1 moles/L of $NH_4H_2PO_4$ and 0.167 moles/L of $CaCl_2$, which is stirred magnetically at 22° C., is used as electrolyte. When pulsed 200 Hz direct current (equal on and off times) and a potential of 6 V are applied, a hydroxyapatite layer is deposited on the titanium panel within 10 minutes. Subsequently, the coated panel is washed twice with deionized water and dried for about 5 minutes in a current of warm air. A coating with a covering density of 2.16 mg/cm$^2$ is produced on the electrode surface by this method.

EXAMPLE 2

As in Example 1, a titanium panel is passivated anodically in 5% phosphoric acid using a current density of 10 mA/cm$^2$ and a potential of about 12 V and subjected to a sol-gel coating procedure by a spraying process using, a solution consisting of 0.05 moles/L of Ti(i-C$_3$H$_7$O)$_4$, 0.04 moles/L of Si(OC$_2$H$_5$)$_4$, 0.01 moles/L of triethyl phosphate and 0.1 moles/L of hydrochloric acid in the form of 37% hydrochloric acid in isopropanol. The hydroxyapatite is deposited as in Example 1 using an electrolyte consisting of 0.1 moles/L Ca(NO$_3$)$_2$ and 0.06 moles/L Na$_2$HPO$_4$.

EXAMPLE 3

As in Example 1, a titanium panel is subjected twice to a sol-gel treatment by the dip coating technique (withdrawal rate of 1cm/min) using a solution consisting of 0.05 moles/L of Ti(i-C$_3$H$_7$O)$_4$, 0.05 moles/L of Si(OC$_2$H$_5$)$_4$, and 0.1 moles/L of hydrochloric acid in the form of a solution of 37% hydrochloric acid in isopropanol. After about 6 hours, hydroxyapatite is deposited electrochemically under the conditions of Example 1, but at 40° C.

EXAMPLE 4

A titanium panel is treated as in Example 3. In addition, there is a further dip coating procedure in a solution consisting of 0.025 moles/L of Ti(i-C$_3$H$_7$O)$_4$, 0.025 moles/L of Si(OC$_2$H$_5$)$_4$, and 0.05 moles/L of hydrochloric acid in the form of a 37% solution of hydrochloric acid in isopropanol and 0.05 moles/L of CaCl$_2$.2H$_2$O in ethanol. After about 4 hours, hydroxyapatite is deposited electrochemically under the conditions of Example 1, but at 180 Hz.

EXAMPLE 5

As in Example 1, a titanium panel is subjected twice to a sol-gel treatment by the dip coating technique (withdrawal rate of 1 cm/min) using, a solution consisting of 0.033 moles/L of Ti(i-C$_3$H$_7$O)$_4$, 0.033 moles/L of Si(OC$_2$H$_5$)$_4$, 0.033 moles/L of Al(i-C$_4$H$_9$O)$_3$ and 0.1 moles/L of hydrochloric acid in the form of a 37% solution of hydrochloric acid in isopropanol. In addition, there is a further dip coating procedure using a solution consisting of 0.0167 moles/L of Ti(i-C$_3$H$_7$O)$_4$, 0.0167 moles/L of Si(OC$_2$H$_5$)$_4$, 0.0167 moles/L of Al(i-C$_4$H$_9$O)$_3$ and 0.1 moles/L of hydrochloric acid in the form of a 37% solution of hydrochloric acid in isopropanol and 0.05 moles/L of CaCl$_2$.2H$_2$O in ethanol. After about 4 hours, hydroxyapatite is deposited electrochemically under the conditions of Example 1, but at 50 Hz and 3.8 V. During 7 minutes, a coating density of 1.98 mg/cm$^2$ is attained.

EXAMPLE 6

A glass plate, having the dimensions of 80×20×1 mm and coated with 2 µm of titanium, is pretreated as in Example 5 and coated with hydroxyapatite. A scanning electron microscope photograph (5 kV) of a fractured edge preparation shows that the average height of the coating is 15 µm.

EXAMPLE 7

A glass plate, coated with 2.5 µm of TiN, is treated as in Example 6. A scanning electron microscope photograph (5 kV) of a fractured edge preparation shows that the average height of the coating is 10 µm.

EXAMPLE 8

A high-grade steel panel, having the dimensions of 80×20×1 mm and coated with 2 µm of TiN, is subjected to a sol-gel treatment by the dip coating technique (withdrawal rate of 1 cm/min) using a solution consisting of 0.033 moles/L of Ti(i-C$_3$H$_7$O)$_4$, 0.033 moles/L of Si(OC$_2$H$_5$)$_4$, 0.033 moles/L of Al(i-C$_4$H$_9$O)$_3$ and 0.1 moles/L of hydrochloric acid in the form of a 37% solution of hydrochloric acid in isopropanol. In addition, there is a further dip coating procedure using a solution consisting of 0.0167 moles/L of Ti(i-C$_3$H$_7$O)$_4$, 0.0167 moles/L of Si(OC$_2$H$_5$)$_4$, 0.016 moles/L of Al(i-C$_4$H$_9$O)$_3$ and 0.1 moles/L of hydrochloric acid in the form of a 37% solution of hydrochloric acid in isopropanol and 0.05 moles/L of CaCl$_2$.2H$_2$O in ethanol. After about 4 hours, hydroxyapatite is deposited electrochemically under the conditions of Example 1, but at 50 Hz and 3.5 V. During, 5 minutes, a coating density of 1.46 mg/cm$_2$ is attained.

EXAMPLE 9

A high-grade steel panel, having the dimensions of 80×20×1 mm and coated with 2 µm of TiN, is subjected to a sol-gel treatment by the dip coating technique (withdrawal rate of 1 cm/min) using a solution consisting of 0.05 moles/L of Ti(i-C$_3$H$_7$O)$_4$, 0.05 moles/L of Si(OC$_2$H$_5$)$_4$ and 0.1 moles/L of hydrochloric acid in the form of a 37% solution of hydrochloric acid in isopropanol. In addition, there is a further dip coating procedure using a solution consisting of 0.025 moles/L of Ti(i-C$_3$H$_7$O)$_4$, 0.025 moles/L of Si(OC$_2$H$_5$)$_4$ and 0.05 moles/L of hydrochloric acid in the form of a 37% solution of hydrochloric acid in isopropanol and 0.05 moles/L of CaCl$_2$.2H$_2$O in ethanol. After about 4 hours, hydroxyapatite is deposited electro-chemically under the conditions of Example 1, but at 50 Hz, 4 V and 35° C.

EXAMPLE 10

A high-grade steel panel, coated with 2.2 µm of TiN, is pretreated as in Example 8. After about 4 hours, the hydroxyapatite is deposited electrochemically under the conditions of Example 1, but at 50 Hz, 3.8 V and 25° C. During 8 minutes, a covering density of 1.58 mg/cm$_2$ is achieved. A mechanically abraded coating sample is dried for 2 hours at 200° C., dissolved in concentrated hydrochloric acid and analyzed spectrophotometrically (Ca$^{2+}$: arsenic (III) azo method, PO$_4^{3-}$: molybdenum blue method), the calcium to phosphorus ratio is 1.58.

EXAMPLE 11

A polytetrafluoroethylene panel, having the dimensions of 70×20×5 mm and coated with 1.8 µm of TiN, is pretreated as in Example 9. After 4 hours, the hydroxyapatite is deposited electrochemically under the conditions of Example 1, but at 50 Hz, 40 V and 25° C. During 7 minutes, a covering, density of 1.28 mg/cm$^2$ is achieved.

EXAMPLE 12

A high-grade steel panel, coated with 2.4 µm of titanium niobium oxynitride, is pretreated as in Example 9. After 4 hours, the hydroxyapatite is deposited electrochemically under the conditions of Example 1, but at 50 Hz, 3.5 V and 25° C. During 5 minutes, a covering density of 1.32 mg/cm$^2$ is achieved.

EXAMPLE 13

A high-grade steel panel, having the dimensions of 80×20×1 mm and coated with 2 µm of titanium zirconium nitride, is subjected to a sol-gel coating by the dip coating technique (withdrawal rate of 1 cm/min) using a solution consisting of 0.05 moles/L of Ti(i-$C_3H_7O)_4$, 0.05 moles/L of Zr($OC_4H_9)_4$ and 0.1 moles/L of hydrochloric acid in the form of a 37% solution of hydrochloric acid in n-butanol. In addition, there is a further dip coating procedure using a solution consisting of 0.025 moles/L of Ti(i-$C_3H_7O)_4$, 0.025 moles/L of Zr($OC_4H_9)_4$ and 0.05 moles/L of hydrochloric acid in the form of a 37% solution of hydrochloric acid in n-butanol and 0.05 moles/L of $CaCl_2.2H_2O$ in ethanol. After about 4 hours, hydroxyapatite is deposited electrochemically under the conditions of Example 1, but at 50 Hz, 4 V and 25° C.

EXAMPLE 14

A TiAl6V4 disk (14 mm in diameter and 1 mm thick) is subjected to a sol-gel coating procedure by means of ultrasonic fogging (800 kHz, 200 W, nitrogen carrier gas) using the solutions given in Example 8. After 6 hours, hydroxyapatite is deposited electrochemically under the conditions of Example 1, but at 50 Hz, 4 V, 25° C. and with sheet platinum as anode and a platinum wire as the cathode holder.

EXAMPLE 15

A TiAl6V4 disk (14 mm in diameter and 1 mm thick), coated with 2 μm of TiN, is subjected to a sol-gel coating procedure by means of ultrasonic fogging, (800 kHz, 200 W, nitrogen carrier gas) using the solutions named in Example 9. After 6 hours, hydroxyapatite is deposited electrochemically under the conditions of Example 1, but at 50 Hz, 3.5 V, 25° C. and with a high-grade steel clamp as the cathode holder.

EXAMPLE 16

A high-grade steel panel (1.4301), having the dimensions of 80×20×1 mm, is pretreated as in Example 9. After 4 hours, hydroxyapatite is deposited electrochemically under the conditions of Example 1, but at 50 Hz, 4 V, 25° C. and with a high-grade steel chamber as the cathode holder. A covering density of 0.88 mg/cm$^2$ is achieved within 3 minutes.

EXAMPLE 17

The coating preparations, produced in Examples 1 to 16, are tempered for 1 hour at 380° C. under atmospheric conditions. At the same time, there is a loss in weight of the order of 10%. The coatings, so treated, contain carbon as shown by the IR spectra of coating material removed mechanically (v∞at 1450 cm$^{-1}$).

References

1. Radin, S. R. et al.: J. Mater. Sci. Mater in Medicine 1992, 33
2. Ducheyne, P. et al.: J. Biomed. Mater. Res. 1980, 225
3. Arita, I. H. et al.: Mater. Res. Symp. V (San Francisco, Calif.) 1993, Abstr. V2.2
4. Agrawal, D. K. et al.: Mat. Res. Soc. Symp. Proc. Vol. 269, 231 (1992)
5. Brendel, T. et al.: J. Mater. Sci. Mater in Medicine 1992, 175
6. Ducheyne, P. et al.: Biomaterials 1990, 244
7. Lacefield, W. R.: Ann. New York Acad. Sci. 1988, 72
8. Cotell, C. M. et al.: J. Appl. Biomater. 1992, 87
9. WO 92/13984
10. Shirkhanzadeh, M.: J. Mater. Sci. Letters 1993, 16
11. JP 05285212

We claim:

1. A method for electrodepositing hydroxyapatite layers comprising pre-coating a surface of a substrate with a sol-gel having elements of the chemical composition of the surface and/or the hydroxyapatite layer by subjecting the surface to sol-gel coating at least once, and electrochemically depositing hydroxyapatite on the sol-gel coating.

2. The method of claim 1, wherein the substrate to be coated is sufficiently biocompatible for implantation into a human or other animal.

3. The method of claim 1 or 2, wherein the substrate to be coated is metal.

4. The method of claim 3, wherein the metal is selected from the group consisting of titanium, gold and platinum.

5. The method of claim 1 or 2, wherein the substrate to be coated is an iron alloy or a non-ferrous metal alloy.

6. The method of claim 5, wherein the substrate is selected from the group consisting of high grade steel, CoCr$_{28}$Mo and TiAl$_6$V$_4$.

7. The method of claim 1 or 2, wherein the substrate is a ceramic.

8. The method of claim 7, wherein the substrate is selected from the group consisting of oxides, nitrides, oxynitrides and carbonitrides, and the substrate further comprises at least one metal selected from the group consisting of Groups 4 and 5 of the periodic table of the elements.

9. The method of claim 1 or 2, wherein the substrate is monolayer or multilayer coated objects of metals, alloys, ceramics, glasses or plastics.

10. The method of claim 1 or 2, wherein the step of sol-gel coating polymerizes alkoxides or mixtures of alkoxides, and the alkoxides contain an element selected from the group consisting of Groups 3–5 and 13–15 of the periodic table of the elements.

11. The method of claim 7, wherein the step of sol-gel coating polymerizes mixtures of alkoxides, and the mixtures of alkoxides further comprise calcium phosphate ions and/or calcium hydrogen phosphate ions or phosphate esters.

12. The method of claim 1 or 2, further comprising a step of passivation prior to the step of sol-gel coating.

13. The method of claim 1, wherein the electrochemical deposition step is carried out in an electrolysis cell having an inert anode and the precoated substrate as a cathode, using a pulsed direct current with a pulse frequency between 1 and 300 Hz and a voltage between 2 and 10 V.

14. The method of claim 13, wherein an electrolyte is used, and the electrolyte comprises calcium phosphate ions and calcium hydrogen phosphate ions in a molar ratio of approximately 1.5:1 to 1.7:1.

15. The method of claim 13, wherein the anode is carbon or platinum.

16. The method of claim 13, wherein the pulsed direct current used has a pulse frequency of 50 Hz and identical on-off intervals.

17. The method of claim 13, wherein the electrochemical deposition step is carried out at temperatures between 200° and 40° C.

18. The method of claim 1, wherein the coated substrate is subjected to a thermal treatment at temperatures between 300° and 500° C. subsequent to the electrochemical deposition step.

19. The method of claim 1, wherein the step of sol-gel coating uses a process selected from the group consisting of spraying, ultrasonic fogging and dip coating.

20. A substrate coated in accordance with the method of claim 1.

* * * * *